(12) United States Patent
Finkelstein et al.

(10) Patent No.: US 8,148,576 B2
(45) Date of Patent: Apr. 3, 2012

(54) SOLID STATE FORMS OF ALISKIREN COMPOUNDS

(75) Inventors: Nina Finkelstein, Herzliya (IL); Ariel Mittelman, Elad (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 162 days.

(21) Appl. No.: 12/701,295

(22) Filed: Feb. 5, 2010

(65) Prior Publication Data

US 2010/0197793 A1 Aug. 5, 2010

Related U.S. Application Data

(60) Provisional application No. 61/150,196, filed on Feb. 5, 2009.

(51) Int. Cl.
*A61K 31/165* (2006.01)
*C07C 237/14* (2006.01)
*A61P 9/12* (2006.01)

(52) U.S. Cl. ........................ 564/157; 514/616
(58) Field of Classification Search .................. None
See application file for complete search history.

(56) References Cited

U.S. PATENT DOCUMENTS

| 5,559,111 | A  | * | 9/1996 | Goschke et al. ........... 514/227.5 |
| 6,730,798 | B2 |   | 5/2004 | Stutz et al. |
| 2006/0154926 | A1 | | 7/2006 | John et al. |

FOREIGN PATENT DOCUMENTS

| WO | WO 2007/098503 | 8/2007 |
| WO | WO 2007/107317 | 9/2007 |
| WO | WO 2008/055669 | 5/2008 |

OTHER PUBLICATIONS

Lindsay, K.B., et al., *J. Org. Chem.*, vol. 71, pp. 4766-4777 (2006).
Mealy, N.E., et al., *Drugs of the Future*, vol. 26, No. 12, pp. 1139-1148 (2001).

* cited by examiner

*Primary Examiner* — Timothy Thomas
*Assistant Examiner* — Dennis Heyer
(74) *Attorney, Agent, or Firm* — Kenyon & Kenyon LLP

(57) ABSTRACT

The invention relates to solid states of pharmaceutically acceptable compounds of aliskiren, and processes for preparation thereof. The invention further provides pharmaceutical formulations comprising the amorphous or crystalline forms of pharmaceutically acceptable compounds of aliskiren and processes thereof; and a method of inhibiting renin for treating hypertension.

7 Claims, 17 Drawing Sheets

SOLID STATE FORMS OF ALISKIREN COMPOUNDS

CROSS REFERENCE TO RELATED APPLICATIONS

This application claims the benefit of U.S. Provisional Application No. 61/150,196, filed Feb. 5, 2009, herein incorporated by reference in its entirety.

FIELD OF THE INVENTION

The present invention is directed to solid state aliskiren compounds in several forms and methods of preparation thereof.

BACKGROUND OF THE INVENTION

Aliskiren hemifumarate, having the chemical name: (2S,4S,5S,7S)—N-(2-carbamoyl-2-methylpropyl)-5-amino-4-hydroxy-2,7-diisopropyl-8-[4-methoxy-3-(3-methoxypropoxy)phenyl]-octanamide hemifumarate [$C_{30}H_{53}N_3O_6 \cdot 0.5\ C_4H_4O_4$] and the following structure:

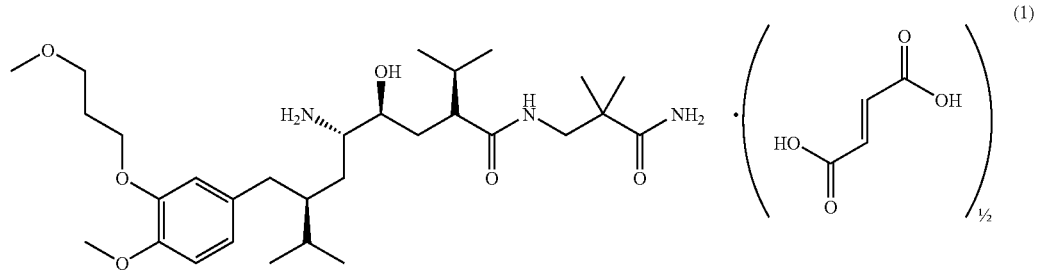

is indicated for treatment of hypertension, acting as a renin inhibitor, and marketed by Novartis as TEKTURNA® in a once-daily formulation. Aliskiren and its related compounds are referred to in U.S. Pat. No. 5,559,111, while synthesis, pharmacological actions, pharmacokinetics and clinical studies of aliskiren and its related compounds are referred to in Lindsay, K. B. et al., *J. Org. Chem.*, Vol. 71, pp 4766-4777 (2006) and in *Drugs of the Future*, Vol. 26, No. 12, pp 1139-1148 (2001).

US publication No. 2006/0154926 (US '926) describes the preparation of aliskiren hydrochloride. Preparation of aliskiren hemifumarate from aliskiren hydrochloride is also described in US '926.

WO2007/107317 describes the preparation of crystalline aliskiren hydrogen sulfate.

WO2007/098503 describes the preparation of crystalline aliskiren nitrate.

WO2008/055669 describes the preparation of crystalline aliskiren orotate.

The present invention discloses solid state forms of aliskiren compounds.

SUMMARY OF THE INVENTION

The present invention provides crystalline forms of pharmaceutically acceptable compounds of aliskiren, namely, aliskiren hemimaleate, aliskiren monomaleate, aliskiren hemisuccinate, aliskiren hemitartrate, aliskiren monotartrate, aliskiren citrate, aliskiren hydrogen citrate, aliskiren dihydrogen citrate, aliskiren hemimalate, aliskiren monomalate, aliskiren hydrogen phosphate, aliskiren hydrogen sulfate, aliskiren dihydrogen phosphate, aliskiren hydrochloride and aliskiren hydrobromide.

The present invention further provides amorphous forms of pharmaceutically acceptable compounds of aliskiren, namely, aliskiren hemimaleate, aliskiren monomaleate, aliskiren hemisuccinate, aliskiren hemitartrate, aliskiren monotartrate, aliskiren citrate, aliskiren hydrogen citrate, aliskiren dihydrogen citrate, aliskiren hemimalate, aliskiren monomalate, aliskiren hydrogen phosphate, aliskiren hydrogen sulfate, aliskiren dihydrogen phosphate, aliskiren hydrochloride and aliskiren hydrobromide.

Solid state forms of the embodiments of the present invention can have at least one or more favorable properties compared with known forms of aliskiren or aliskiren salts. In particular, the solid state forms of the present invention can have improved characteristics such as higher crystallinity, solubility, dissolution rate, morphology, stability to polymorphic conversion, a lower degree of hygroscopicity, storage stability, flowability, and advantageous processing and handling characteristics such as compressibility and/or bulk density. Preferably, the solid state forms of the embodiments of the present invention have advantageous morphology, crystallinity, polymorphic stability, solubility, compressibility and bulk density and/or dissolution rate.

DETAILED DESCRIPTION OF THE INVENTION

As used herein, "room temperature" refers to a temperature of about 15° C. to about 30° C.

In one embodiment, the present invention provides a solid aliskiren hemimaleate.

As used herein, aliskiren hemimaleate refers to a compound composed of aliskiren base and maleic acid having a mol ratio of about 2:1 of aliskiren base to maleic acid, respectively.

Figure 1:
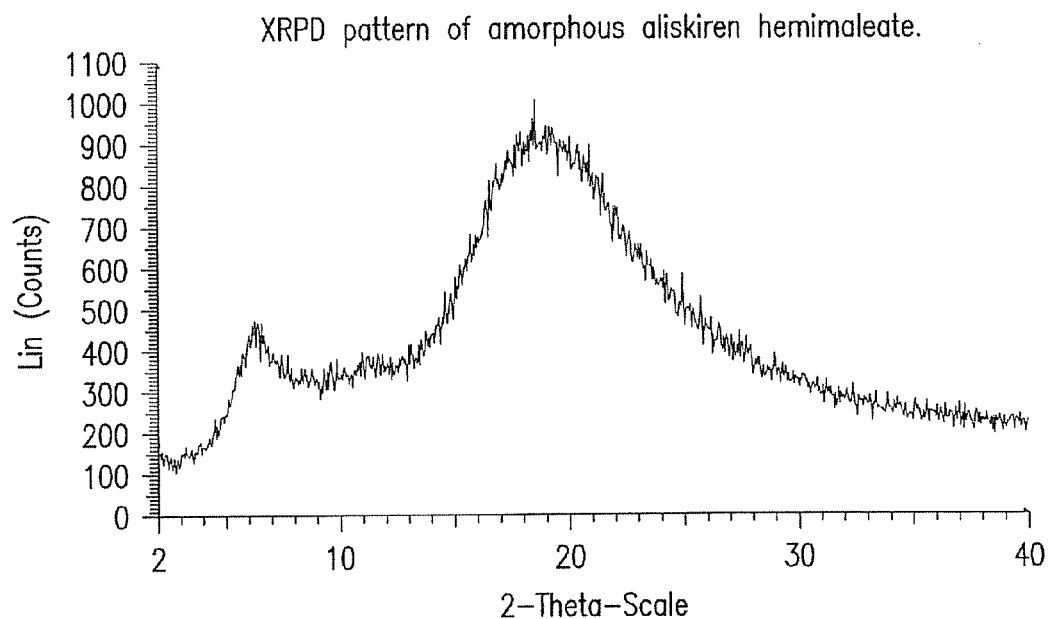
FIG. 1 represents an XRPD pattern of an amorphous aliskiren hemimaleate.

In another embodiment, the invention provides an amorphous aliskiren hemimaleate. The amorphous aliskiren hemimaleate can be characterized by the XRPD pattern depicted in FIG. 1. Typically, the amorphous aliskiren hemimaleate can contain less than about 5%, less than about 3%, or less than about 1% of crystalline aliskiren hemimaleate.

The amorphous aliskiren hemimaleate may be prepared by a process comprising providing a solution of aliskiren base and maleic acid in a $C_1$-$C_2$ alcohol, and further removing the alcohol. The alcohol can be removed for example, by evaporation, at a temperature such as about 20-60° C., about 30-50° C., for example, at about 40° C.

Preferably, the maleic acid is used at a mol ratio of about 2:1 of aliskiren base to maleic acid, respectively.

Preferably, in any embodiment of this process, the aliskiren base is used in an amount of about 20 mg to about 100 mg, for example, about 100 mg per ml of alcohol. The starting aliskiren base used in this process as well as in the other processes can be prepared, for example, according to the procedure described in U.S. Pat. No. 6,730,798 or in U.S. Pat. No. 5,559,111.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren monomaleate.

As used herein, aliskiren monomaleate refers to a compound composed of aliskiren base and maleic acid having a mol ratio of about 1:1 of aliskiren base to maleic acid, respectively.

Figure 2:
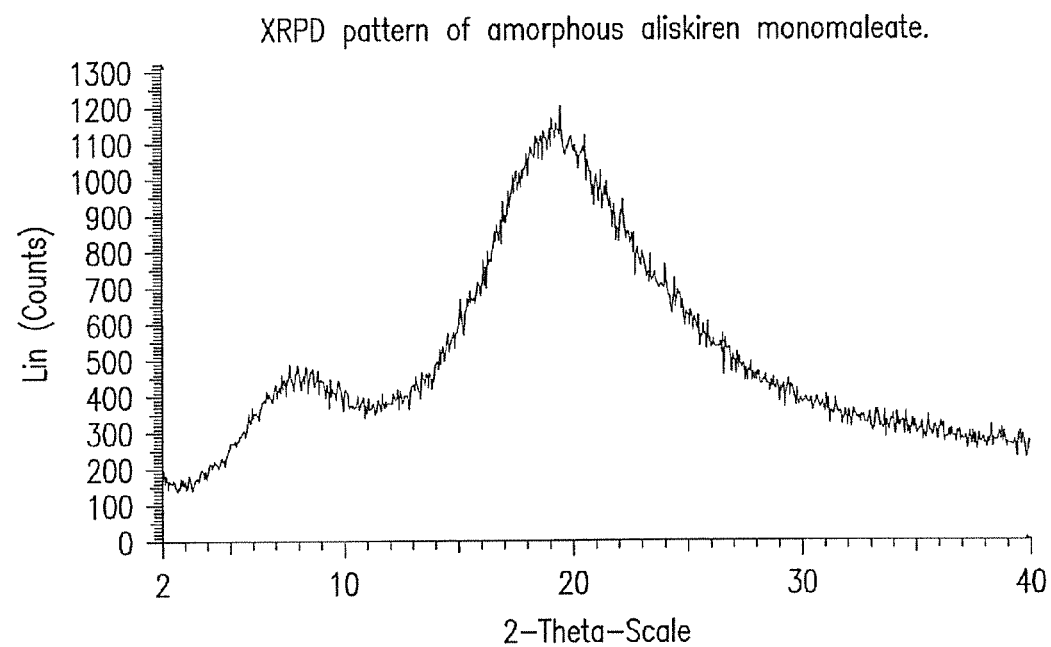
FIG. 2 represents an XRPD pattern of an amorphous aliskiren monomaleate.

In another embodiment, the invention provides an amorphous aliskiren monomaleate. The amorphous aliskiren monomaleate can be characterized by the XRPD pattern depicted in FIG. 2. Typically, the amorphous aliskiren monomaleate can contain less than about 5%, less than about 3%, or less than about 1% of crystalline aliskiren monomaleate.

The amorphous aliskiren monomaleate may be prepared by a process comprising providing a solution of aliskiren base and maleic acid in a $C_1$-$C_2$ alcohol, and further removing the alcohol.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

Preferably, the maleic acid is used at a mol ratio of about 1:1 of aliskiren base to maleic acid.

In one embodiment, the invention provides a solid aliskiren hemisuccinate.

As used herein, aliskiren hemisuccinate refers to a compound composed of aliskiren base and succinic acid having a mol ratio of about 2:1 of aliskiren base to succinic acid, respectively.

Figure 3:
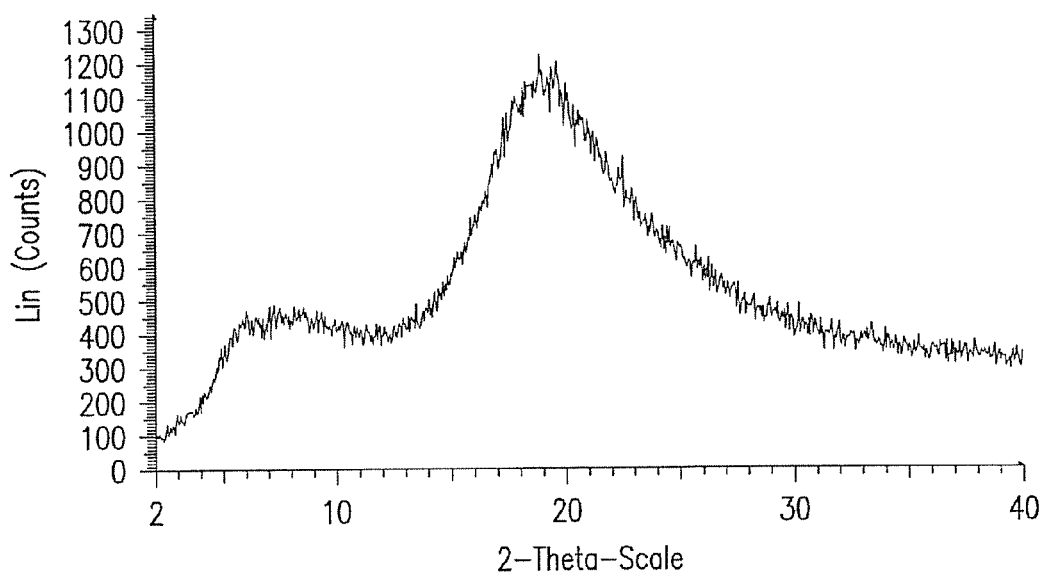
FIG. 3 represents an XRPD pattern of an amorphous aliskiren hemisuccinate.

In another embodiment, the invention provides an amorphous aliskiren hemisuccinate. The amorphous aliskiren hemisuccinate can be characterized by the XRPD pattern depicted in FIG. 3. Typically, the amorphous aliskiren hemisuccinate can contain less than about 5%, less than about 3%, or less than about 1% of crystalline aliskiren hemisuccinate.

The amorphous aliskiren hemisuccinate may be prepared by a process comprising providing a solution of aliskiren base and succinic acid in a $C_1$-$C_2$ alcohol, and further removing the alcohol.

Preferably, the succinic acid is used at a mol ratio of about 2:1 of aliskiren base to succinic acid, respectively.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren hemitartrate.

As used herein, aliskiren hemitartrate refers to a compound composed of aliskiren base and tartaric acid having a mol ratio of about 2:1 of aliskiren base to tartaric acid, respectively.

Figure 4:
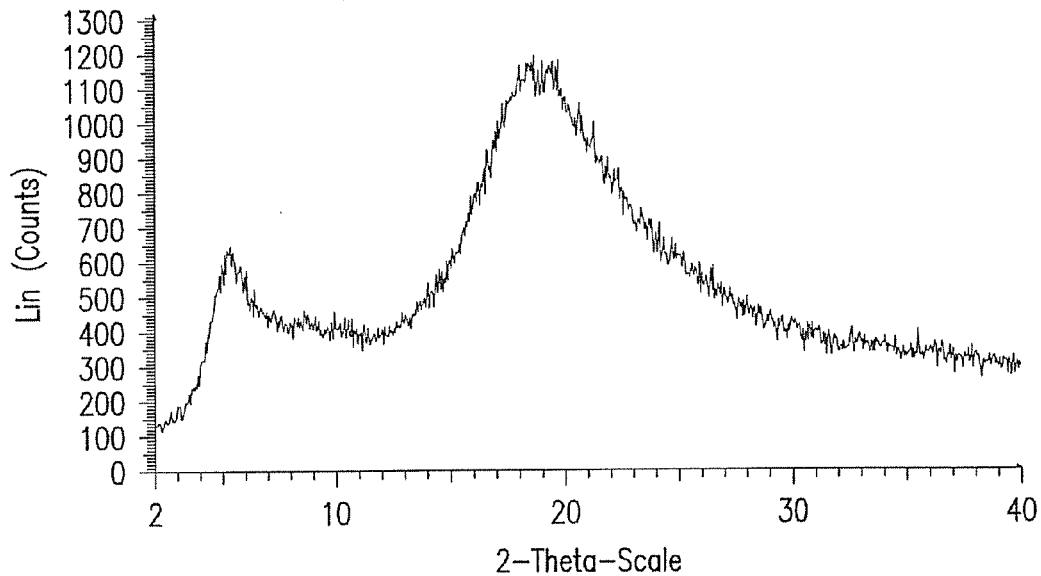
FIG. 4 represents an XRPD pattern of an amorphous aliskiren hemitartrate.

In another embodiment, the invention provides an amorphous aliskiren hemitartrate. The amorphous aliskiren hemitartrate can be characterized by the XRPD pattern depicted in FIG. 4. Typically, the amorphous aliskiren hemitartrate can contain less than about 5%, less than about 3%, or less than about 1% of crystalline aliskiren hemitartrate.

The amorphous aliskiren hemitartrate may be prepared by a process comprising providing a solution of aliskiren base and tartaric acid in a $C_1$-$C_2$ alcohol, and further removing the alcohol.

Preferably, the tartaric acid is used at a mol ratio of about 2:1 of aliskiren base to tartaric acid, respectively.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren monotartrate.

As used herein, aliskiren monotartrate refers to a compound composed of aliskiren base and tartaric acid having a mol ratio of about 1:1 of aliskiren base to tartaric acid.

Figure 5:
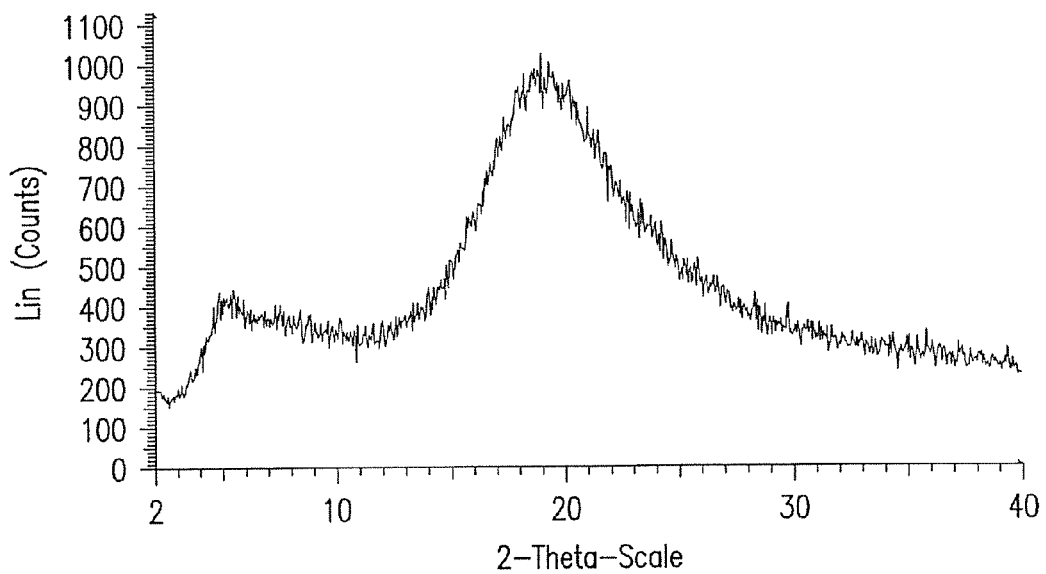
FIG. 5 represents an XRPD pattern of an amorphous aliskiren monotartrate.

In another embodiment, the invention provides an amorphous aliskiren monotartrate. The amorphous aliskiren monotartrate can be characterized by the XRPD pattern depicted in FIG. 5. Typically, the amorphous aliskiren monotartrate can contain less than about 5%, less than about 3%, or less than about 1% of crystalline aliskiren monotartrate.

The amorphous aliskiren monotartrate may be prepared by a process comprising providing a solution of aliskiren base and tartaric acid in a $C_1$-$C_2$ alcohol, and further removing the alcohol.

Preferably, the tartaric acid is used at a mol ratio of about 1:1 of aliskiren base to tartaric acid.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren dihydrogen citrate.

As used herein, aliskiren dihydrogen citrate refers to a compound composed of aliskiren and citric acid having a mol ratio of about 1:1 of aliskiren base to citric acid.

Figure 6:
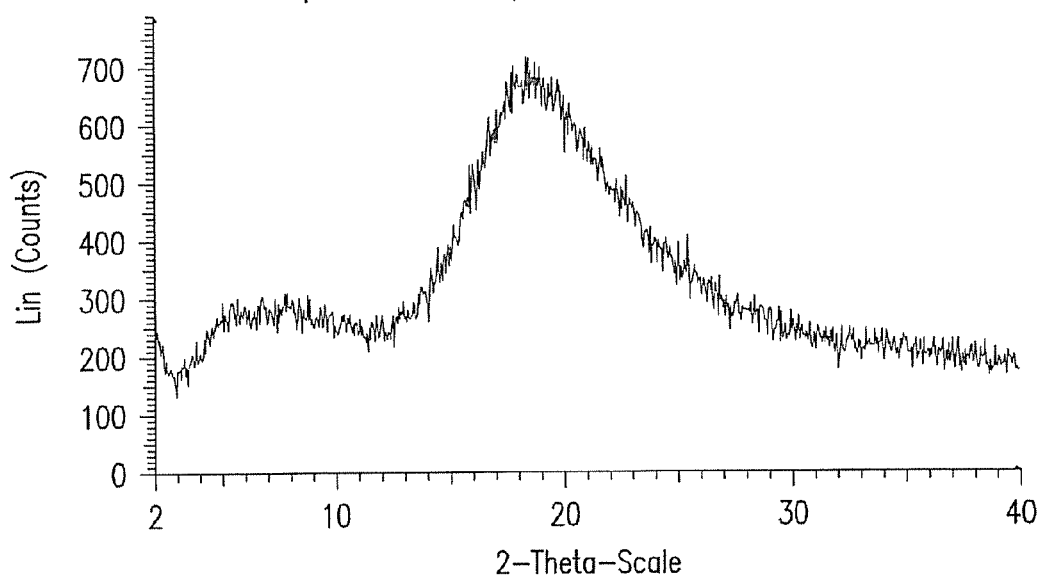
FIG. 6 represents an XRPD pattern of an amorphous aliskiren dihydrogen citrate.

In another embodiment, the invention provides an amorphous aliskiren dihydrogen citrate. The amorphous aliskiren dihydrogen citrate can be characterized by the XRPD pattern depicted in FIG. 6. Typically, the amorphous aliskiren dihydrogen citrate can contain less than about 5%, less than about 3%, or less than about 1% of crystalline aliskiren dihydrogen citrate.

The amorphous aliskiren dihydrogen citrate may be prepared by a process comprising providing a solution of aliskiren base and citric acid in a $C_1$-$C_2$ alcohol, and further removing the alcohol.

Preferably, the citric acid is used at a mol ratio of about 1:1 of aliskiren base to citric acid.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren hydrogen citrate.

As used herein, aliskiren hydrogen citrate refers to a compound composed of aliskiren and citric acid having a mol ratio of about 1:2/3 aliskiren base to citric acid, respectively.

Figure 7:
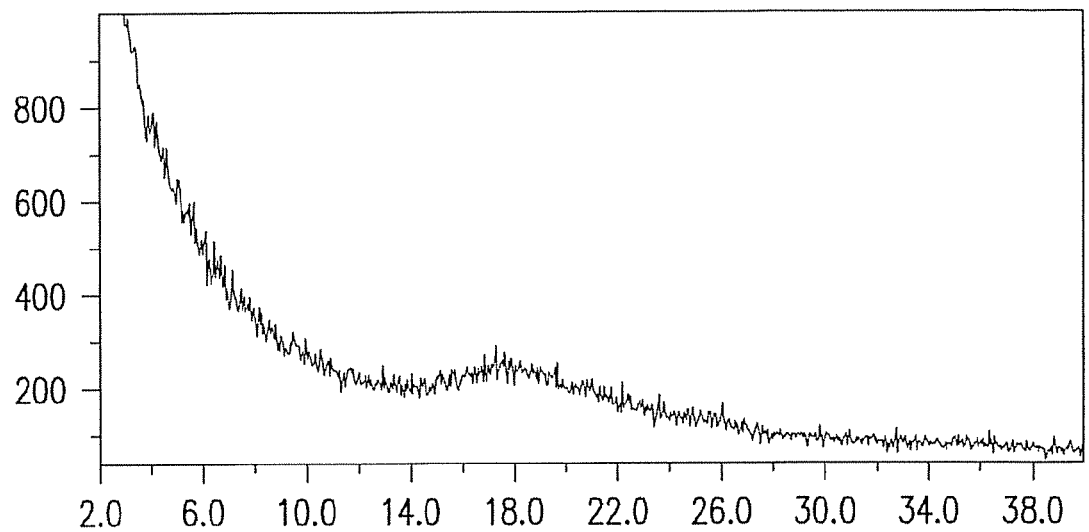
FIG. 7 represents an XRPD pattern of an amorphous aliskiren hydrogen citrate.

In another embodiment, the invention provides an amorphous aliskiren hydrogen citrate. The amorphous aliskiren hydrogen citrate can be characterized by the XRPD pattern depicted in FIG. 7. Typically, the amorphous aliskiren hydrogen citrate can contain less than about 5%, less than about 3%, or less than about 1% of crystalline aliskiren hydrogen citrate.

The amorphous aliskiren hydrogen citrate may be prepared by a process comprising providing a solution of aliskiren base and citric acid in a $C_1$-$C_2$ alcohol, and further removing the alcohol.

Preferably, the citric acid is used at a mol ratio of about 1:2/3 of aliskiren base to citric acid, respectively.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

As used herein, aliskiren citrate refers to a compound composed of aliskiren and citric acid having a mol ratio of about 1:1/3 of aliskiren base to citric acid, respectively.

Figure 8:
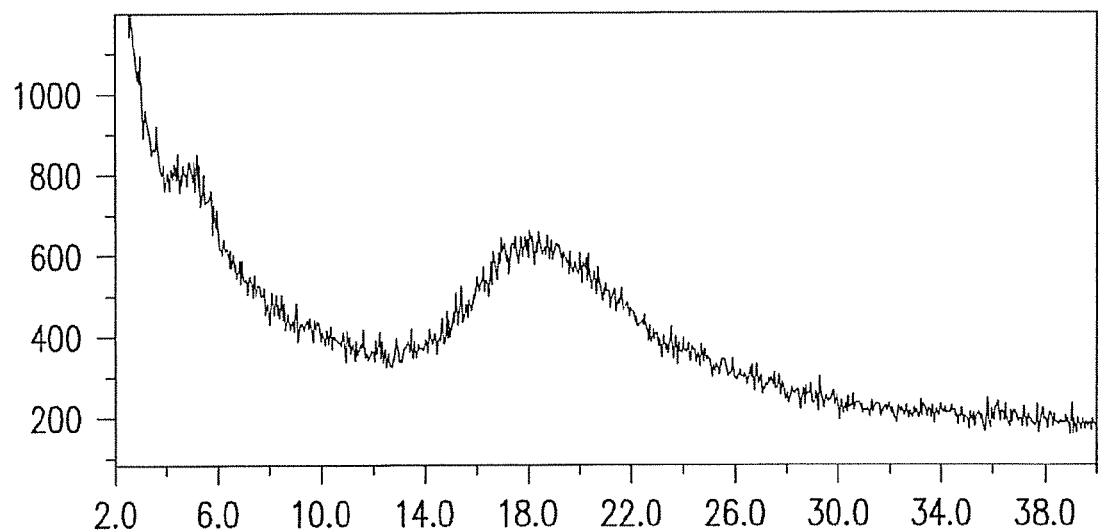
FIG. 8 represents an XRPD pattern of an amorphous aliskiren citrate.

In another embodiment, the invention provides an amorphous aliskiren citrate. The amorphous aliskiren citrate can be characterized by the XRPD pattern depicted in FIG. 8. Typically, the amorphous aliskiren citrate can contain less than about 5%, less than about 3%, or less than about 1% of crystalline aliskiren citrate.

The amorphous aliskiren citrate may be prepared by a process comprising providing a solution of aliskiren base and citric acid in a $C_1$-$C_2$ alcohol, and further removing the alcohol.

Preferably, the citric acid is used at a mol ratio of about 1:1/3 of aliskiren base to citric acid, respectively.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren hemimalate.

As used herein, aliskiren hemimalate refers to a compound composed of aliskiren and malic acid having a mol ratio of about 2:1 of aliskiren base to malic acid, respectively.

Figure 9:
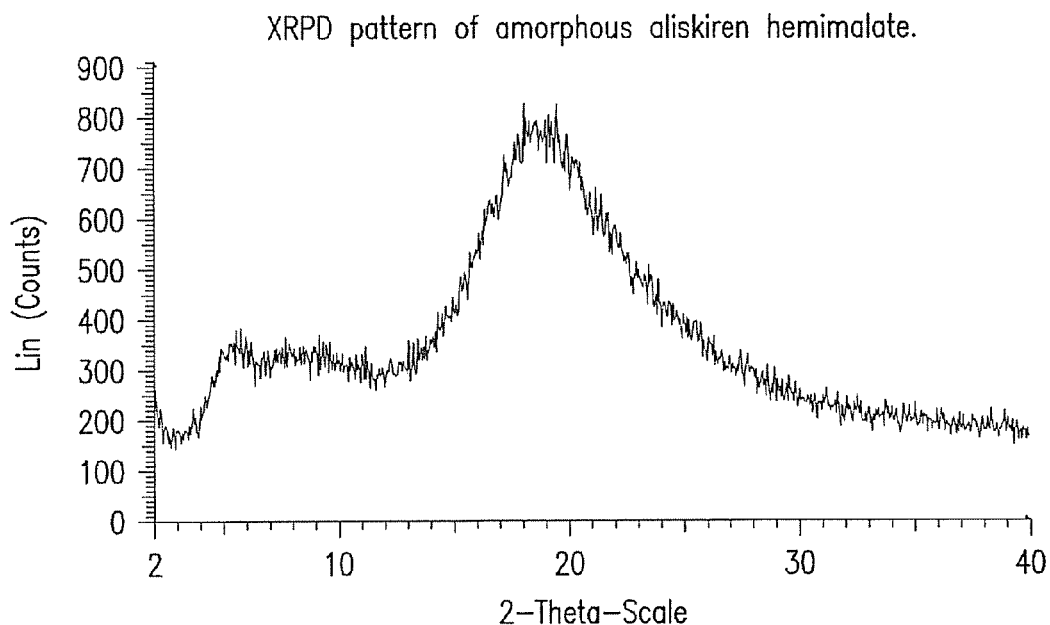
FIG. 9 represents an XRPD pattern of an amorphous aliskiren hemimalate.

In another embodiment, the invention provides an amorphous aliskiren hemimalate. The amorphous aliskiren hemimalate can be characterized by the XRPD pattern depicted in FIG. 9. Typically, the amorphous aliskiren hemimalate can contain less than about 5%, less than about 3%, or less than about 1% of crystalline aliskiren hemimalate.

The amorphous aliskiren hemimalate may be prepared by a process comprising providing a solution of aliskiren base and malic acid in a $C_1$-$C_2$ alcohol, and further removing the alcohol.

Preferably, the malic acid is used at a mol ratio of about 2:1 of aliskiren base to malic acid, respectively.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren monomalate.

As used herein, aliskiren monomalate refers to a compound composed of aliskiren and malic acid having a mol ratio of about 1:1 of aliskiren base:malic acid.

Figure 10:
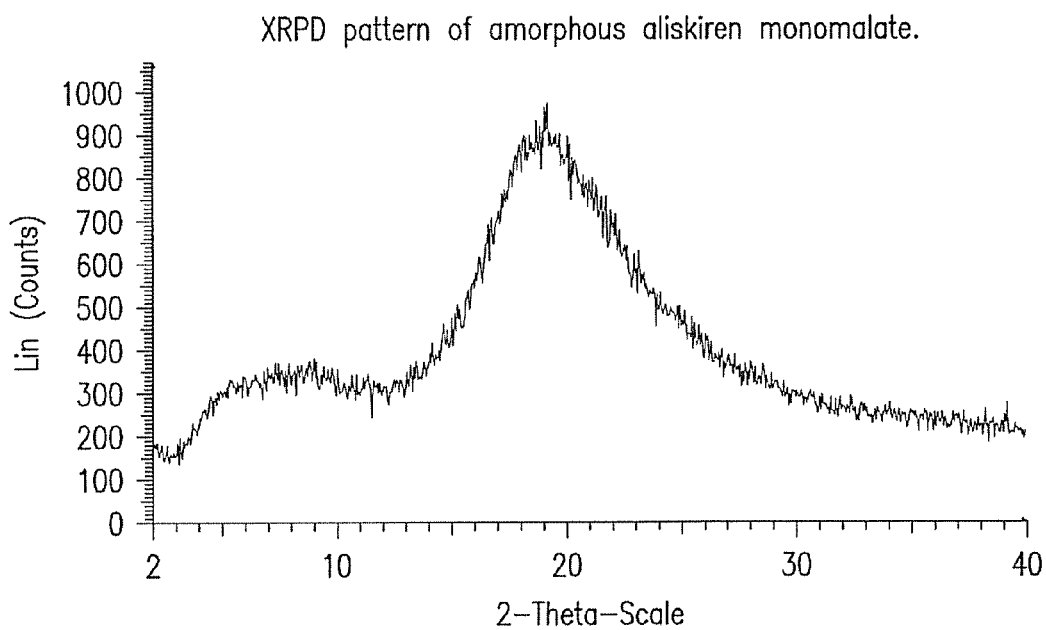
FIG. 10 represents an XRPD pattern of an amorphous aliskiren monomalate.

In another embodiment, the invention provides an amorphous aliskiren monomalate. The amorphous aliskiren monomalate can be characterized by the XRPD pattern depicted in FIG. 10. Typically, the amorphous aliskiren monomalate can contain less than about 5%, less than about 3%, or less than about 1% of crystalline aliskiren monomalate.

The amorphous aliskiren monomalate may be prepared by a process comprising providing a solution of aliskiren base and malic acid in a $C_1$-$C_2$ alcohol, and further removing the alcohol.

Preferably, the malic acid is used at a mol ratio of about 1:1 of aliskiren base to malic acid.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren hydrogen phosphate.

As used herein, aliskiren hydrogen phosphate refers to a compound composed of aliskiren and ortho-phosphoric acid having a mol ratio of about 1:2/3 of aliskiren base to ortho-phosphoric acid, respectively.

Figure 11:
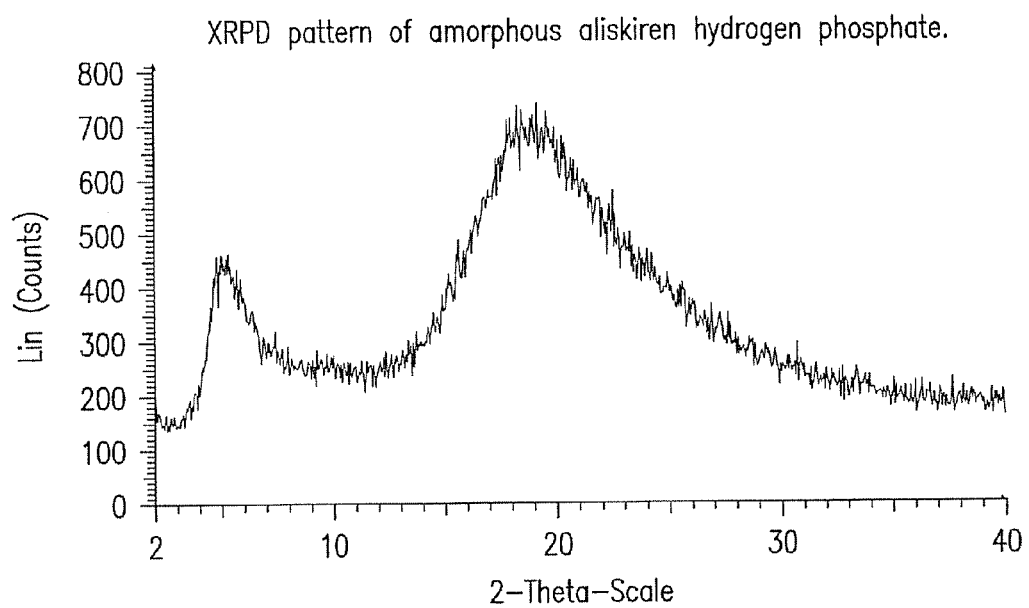
FIG. 11 represents an XRPD pattern of an amorphous aliskiren hydrogen phosphate.

In another embodiment, the invention provides an amorphous aliskiren hydrogen phosphate. The amorphous aliskiren hydrogen phosphate can be characterized by the XRPD diffraction pattern depicted in FIG. 11. Typically, the amorphous aliskiren hydrogen phosphate can contain less than about 5%, less than about 3%, or less than about 1% of crystalline aliskiren hydrogen phosphate.

The amorphous aliskiren hydrogen phosphate may be prepared by a process comprising; providing a solution of aliskiren base and ortho-phosphoric acid in a $C_1$-$C_2$ alcohol, and further removing the alcohol.

Preferably, the ortho-phosphoric acid is used at a mol ratio of about 1:2/3 of aliskiren base to ortho-phosphoric acid, respectively.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren dihydrogen phosphate.

As used herein, aliskiren dihydrogen phosphate refers to a compound composed of aliskiren and ortho-phosphoric acid having a mol ratio of about 1:1 of aliskiren base to ortho-phosphoric acid.

Figure 12:
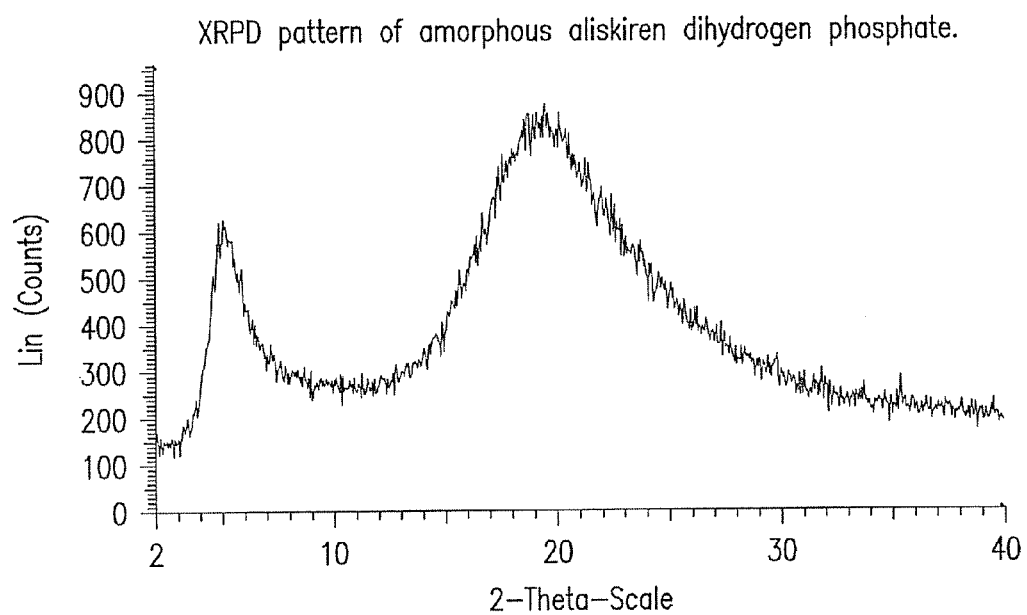
FIG. 12 represents an XRPD pattern of an amorphous aliskiren dihydrogen phosphate.

In another embodiment, the invention provides an amorphous aliskiren dihydrogen phosphate. The amorphous aliskiren dihydrogen phosphate can be characterized by the XRPD pattern depicted in FIG. 12. Typically, the amorphous aliskiren dihydrogen phosphate can contain less than about 5%, less than about 3% crystallinity, or less than about 1% of crystalline aliskiren dihydrogen phosphate.

The amorphous aliskiren dihydrogen phosphate may be prepared by a process comprising providing a solution of aliskiren base and ortho-phosphoric acid in a $C_1$-$C_2$ alcohol, and further removing the alcohol.

Preferably, the ortho-phosphoric acid is used at a mol ratio of about 1:1 of aliskiren base to ortho-phosphoric acid.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

As used herein, aliskiren hydrochloride refers to a compound composed of aliskiren and hydrogen chloride having a mol ratio of about 1:1 of aliskiren base to hydrogen chloride.

Figure 13:
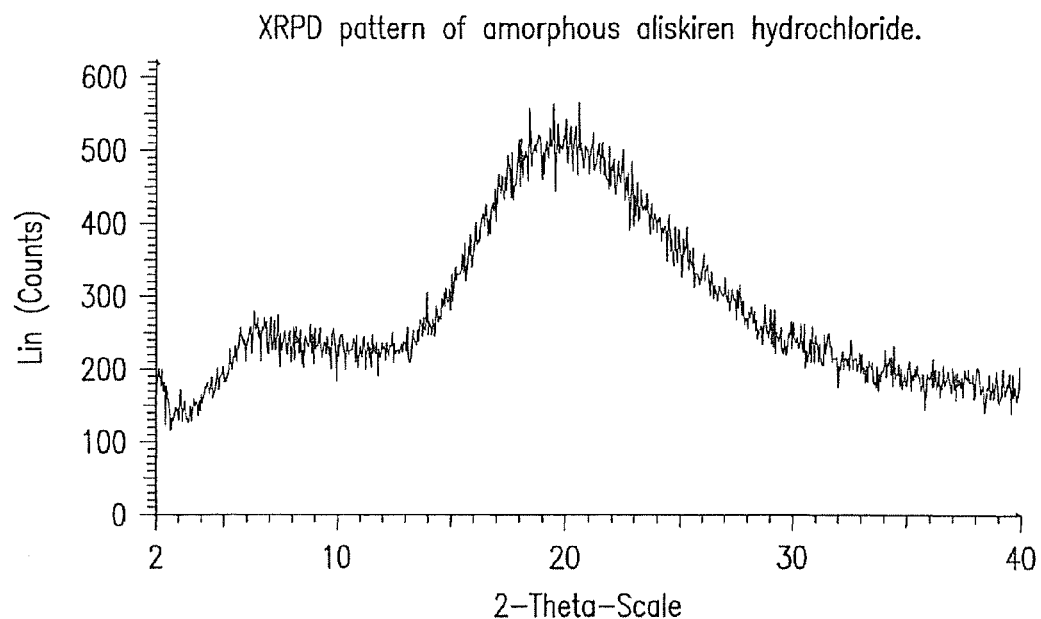
FIG. 13 represents an XRPD pattern of an amorphous aliskiren hydrochloride.

In yet another embodiment, the invention provides an amorphous aliskiren hydrochloride. The amorphous aliskiren hydrochloride can be characterized by the XRPD pattern depicted in FIG. 13. Typically, the amorphous aliskiren hydrochloride can contain less than about 5%, less than about 3% crystallinity, or less than about 1% of crystalline aliskiren hydrochloride.

The amorphous aliskiren hydrochloride may be prepared by a process comprising providing a solution of aliskiren base and hydrochloric acid in a $C_1$-$C_2$ alcohol, and further removing the alcohol.

Preferably, the hydrochloric acid is used at a mol ratio of about 1:1 of aliskiren base to hydrogen chloride.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

In one embodiment, the invention provides a solid aliskiren hydrobromide.

As used herein, aliskiren hydrobromide refers to a compound composed of aliskiren and hydrobromic acid having a mol ratio of about 1:1 of aliskiren base to hydrogen bromide.

Figure 14:
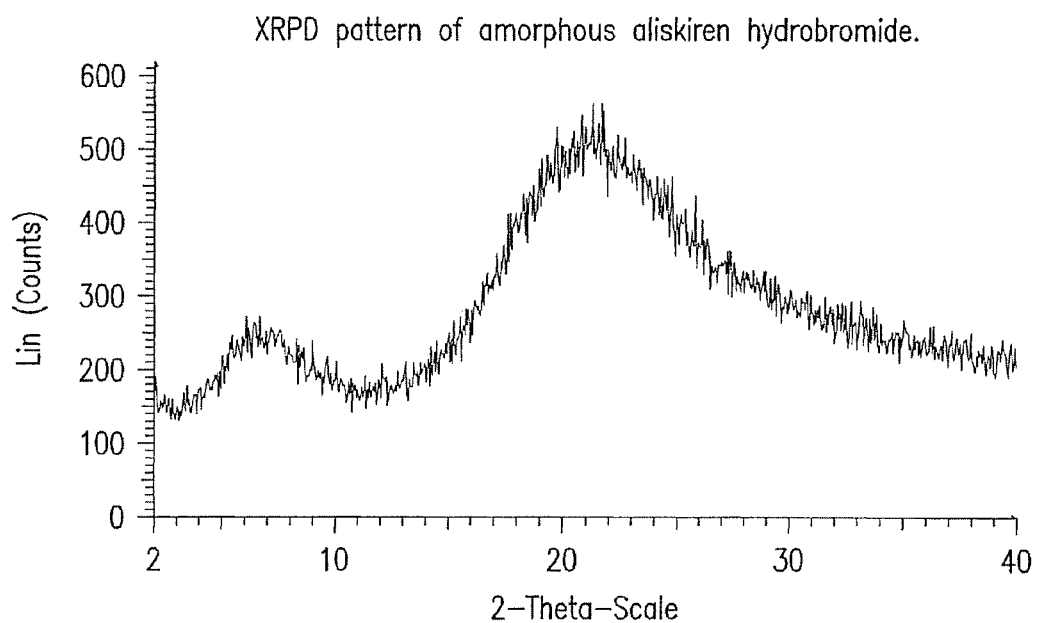
FIG. 14 represents an XRPD pattern of an amorphous aliskiren hydrobromide.

In yet another embodiment, the invention provides an amorphous aliskiren hydrobromide. The amorphous aliskiren hydrobromide can be characterized by the XRPD pattern depicted in FIG. 14. Typically, the amorphous aliskiren hydrobromide can contain less than about 5%, less than about 3%, or less than about 1% of crystalline aliskiren hydrobromide.

The amorphous aliskiren hydrobromide may be prepared by a process comprising providing a solution of aliskiren base and hydrogen bromide in a $C_1$-$C_2$ alcohol, and further removing the alcohol.

Preferably, the hydrogen bromide is used at a mol ratio of about 1:1 of aliskiren base to hydrogen bromide.

Preferably, in any embodiment of this process, the aliskiren base is used in an amount of about 20 mg to about 100 mg, for example, about 100 mg per ml of alcohol.

The solution can be maintained for about 5 minutes to about an hour, at a temperature such as about 15° C. to about 60° C., for example, at about room temperature.

The obtained product is preferably dried. Drying is preferably carried out under a pressure of less than one atmosphere (reduced pressure), including a pressure of less than about 100 mm Hg. Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, about 16 hours to about 48 hours, or about 16 hours to about 24 hours.

Preferably, any acid used in any of the processes described above is introduced to the reaction while it is dissolved in a $C_1$-$C_2$ alcohol. Thus, HCl and HBr are preferably used in the form of a gaseous solution of HCl/HBr in the alcohol.

Figure 15:
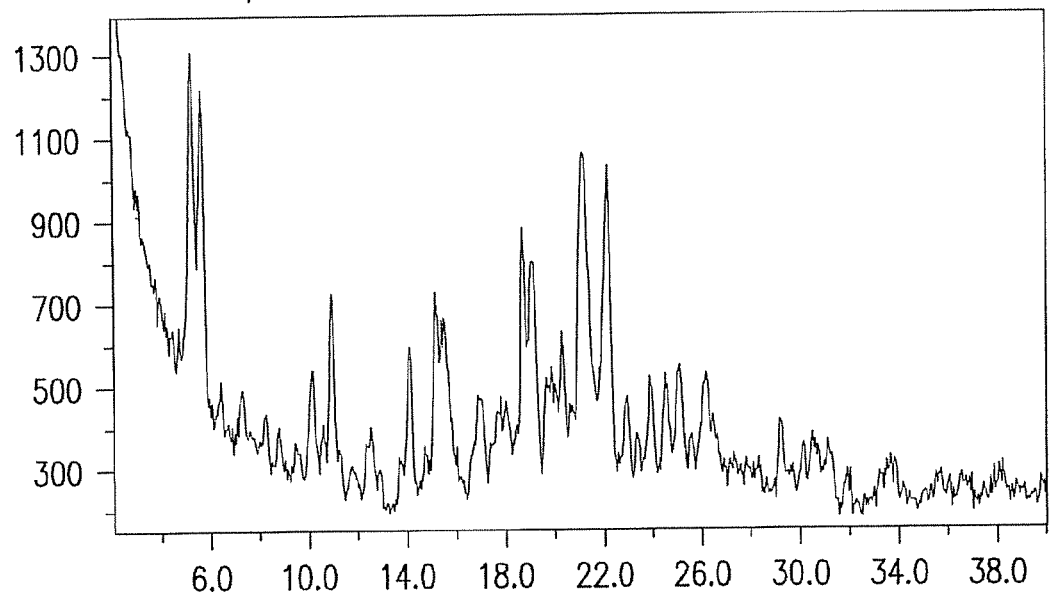
FIG. 15 represents an XRPD pattern of crystalline Form C1 of aliskiren hydrochloride.

In one embodiment, the present invention provides a crystalline form of aliskiren hydrochloride, designated C1, characterized by data selected from the group consisting of an XRPD pattern with peaks at about 5.3, 14.1, 18.7, 21.2 and 22.2±0.2 degrees two-theta; an XRPD pattern as depicted in FIG. 15; and combination thereof.

Form C1 can be further characterized by an XRPD pattern containing additional peaks at about 5.7, 10.1, 10.9, 15.2 and 19.1±0.2 degrees two-theta.

Aliskiren hydrochloride C1 can be prepared by a process comprising providing a slurry or a solution of aliskiren hydrochloride in isobutyl acetate and recovering the crystalline material from either of them; wherein if slurry is provided the starting aliskiren hydrochloride is in an amorphous form.

Preferably, in any embodiment of this process, the aliskiren base is used in an amount of about 20 mg to about 100 mg, more preferably about 100 mg per ml of alcohol.

The slurry or the solution is maintained prior to the recovery of the crystalline material, for example, for about 24 hours to about 72 hours, preferably at about room temperature. The recovery of the crystalline material can include precipitating from the solution followed by filtration, or filtration from the slurry. Precipitation can be induced, for example, by cooling.

Figure 16:
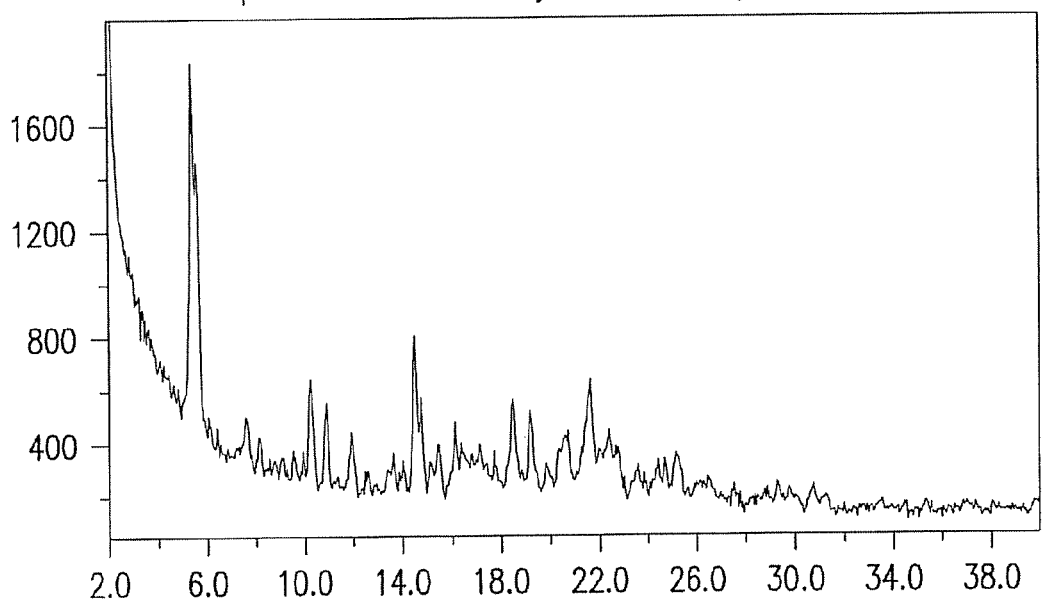
FIG. 16 represents an XRPD pattern of crystalline Form C2 of aliskiren hydrochloride.

In another embodiment, the invention provides aliskiren hydrochloride, designated C2, characterized by data selected from the group consisting of an XRPD pattern with peaks at about 5.4, 11.9, 14.5, 16.1 and 21.6±0.2 degrees two-theta; an XRPD pattern as depicted in FIG. 16; and combination thereof.

Form C2 can be further characterized by an XRPD pattern containing additional peaks at about 5.6, 10.2, 14.8, 18.5 and 19.2±0.2 degrees two-theta.

Aliskiren hydrochloride C2 can be prepared by a process comprising providing a slurry or a solution of aliskiren hydrochloride in a solvent selected from the group consisting of toluene, dimethylcarbonate, and chlorobenzene, and recovering the crystalline material from either of them; wherein, if slurry is provided the starting aliskiren hydrochloride is amorphous.

The obtained aliskiren hydrochloride Form C2 can be further dried for example, for about 16 hours to about 72 hours, about 16 hours to about 48 hours, about 16 hours to about 24 hours. Drying can be performed under vacuum at about 40° C. to about 50° C.

The aliskiren base can be used in an amount of about 20 mg to about 100 mg, for example, about 100 mg per ml of alcohol.

The slurry or the solution can be maintained for about 24 hours to about 72 hours, preferably at about room temperature.

Aliskiren hydrochloride C2 can be prepared by another process comprising providing a slurry or a solution of aliskiren hydrochloride in chlorobenzene, further stirring the solution to obtain a suspension and removing the solvent to obtain the crystalline form aliskiren hydrochloride C2; wherein, if a slurry is provided, the starting aliskiren hydrochloride is amorphous.

Stirring is performed for a period of about one day to about three days or, if solution is provided, until a suspension is obtained.

Figure 17:
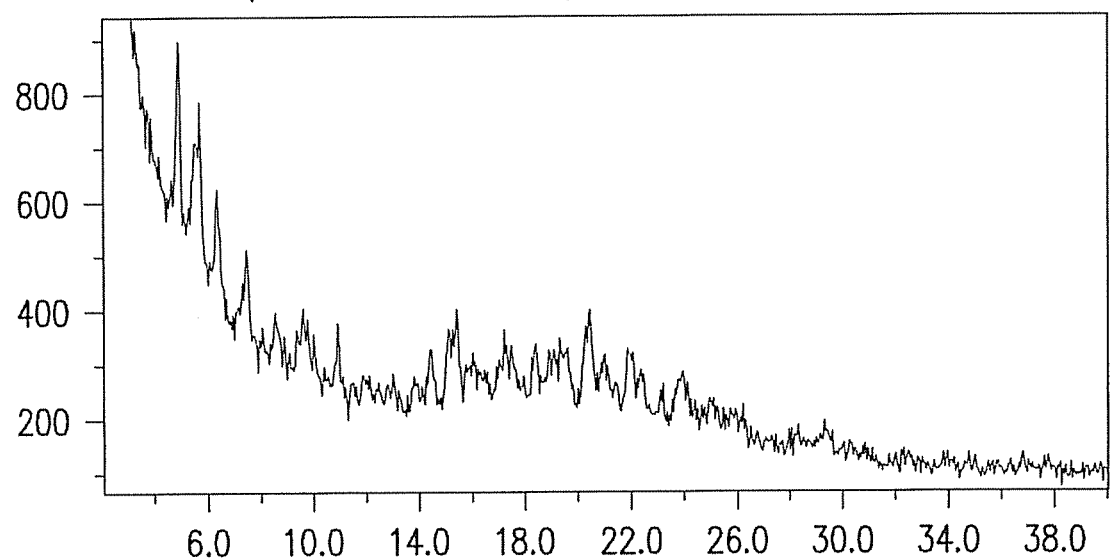
FIG. 17 represents an XRPD pattern of crystalline Form C3 of aliskiren hydrochloride.

In one embodiment, the invention provides aliskiren hydrochloride, designated C3, characterized by data selected from the group consisting of an XRPD pattern with peaks at about 4.9, 6.3, 7.5, 9.6 and 17.2±0.2 degrees two-theta; an XRPD pattern as depicted in FIG. 17; and combination thereof.

Form C3 can be further characterized by additional peaks at about 5.7, 14.4, 15.4, 20.4 and 21.9±0.2 degrees two-theta.

Aliskiren hydrochloride C3 can be prepared by a process comprising drying aliskiren hydrochloride C1.

Drying can be carried out under a pressure of less than one atmosphere (reduced pressure), including a pressure of less than about 100 mm Hg. Drying can be carried out by heating, with or without reducing the pressure, at about 30° C. to about 80° C., about 30° C. to about 60° C., at about 40° C. to about 50° C., for example, at about 40° C. The obtained precipitate can be dried for about 16 hours to about 72 hours, for about 16 hours to about 48 hours, for about 16 hours to about 24 hours.

Figure 18:
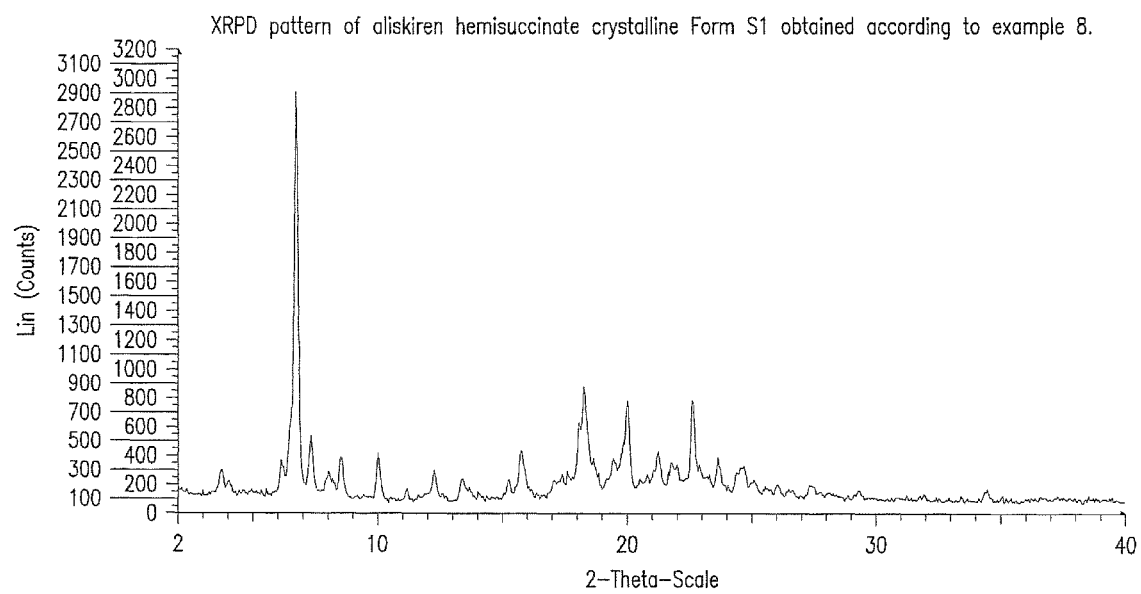
FIG. 18 represents an XRPD pattern of crystalline Form S1 of aliskiren hemisuccinate obtained according to example 8.
Figure 19:
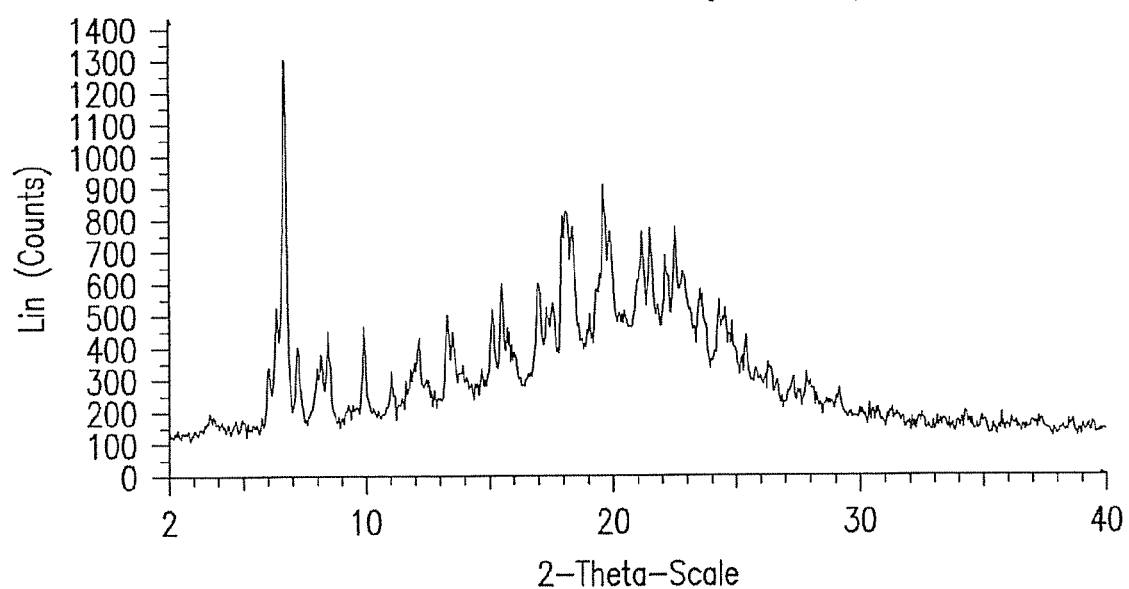
FIG. 19 represents an XRPD pattern of crystalline Form S1 of aliskiren hemisuccinate obtained according to example 10.
Figure 20:
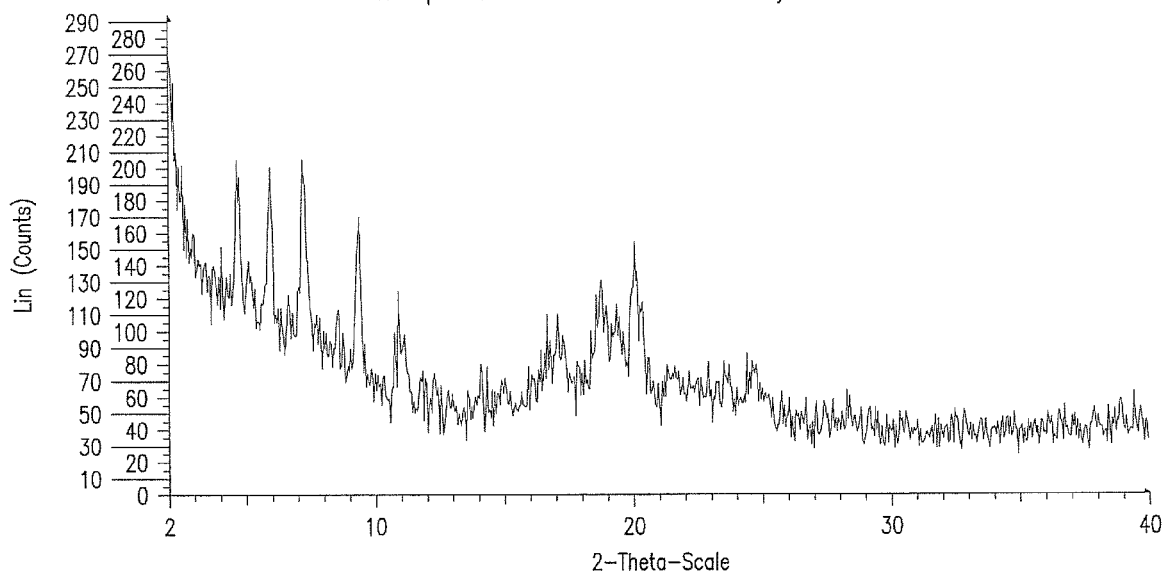
FIG. 20 represents an XRPD pattern of crystalline Form S2 of aliskiren hemisuccinate.

In one embodiment, the invention provides aliskiren hemisuccinate, designated S1, characterized by data selected form the group consisting of an XRPD pattern with peaks at about 3.7, 6.7, 7.3 and 8.5±0.2 degrees two-theta; an XRPD pattern as depicted in FIG. 18; and combination thereof.

Form S1 can be further characterized by additional peaks at about 8.0, 10.0, 13.4 and 22.6±0.2 degrees two-theta.

In another embodiment, Form S1 is characterized by an XRPD pattern with peaks at about 8.4, 9.9, 18.2, 20.0 and 22.6±0.3 degrees two-theta.

In another embodiment, Form S1 is characterized by an XRPD pattern with peaks at about 6.1, 7.2, 8.4, 9.9, 12.2, 15.2, 18.2, 20.0, 21.2 and 22.6±0.3 degrees two-theta.

Aliskiren hemisuccinate Form S1 typically has one or more improved characteristics compared to the prior art forms, especially compared with the known aliskiren hemifumarate forms, such as: higher crystallinity, solubility, dissolution rate, morphology, stability to polymorphic conversion, a lower degree of hygroscopicity, storage stability, flowability, and advantageous processing and handling characteristics such as compressibility and/or bulk density. Aliskiren hemisuccinate Form S1 preferably has an advantageous crystallinity or solubility compared to known forms of aliskiren salts (especially compared with known aliskiren hemifumarate forms). In particular aliskiren hemisuccinate Form S1 has a crystal habit that enables easy handling and processing, and thus can be easily compressed.

Form S1 can be prepared by a process comprising providing a solution aliskiren hemisuccinate in a solvent selected from the group consisting of dimethylcarbonate and diethylcarbonate, further stirring the solution to obtain a suspension and recovering the crystalline material.

The aliskiren hemisuccinate can be used in an amount of about 20 mg to about 100 mg, for example, about 100 mg per ml of solvent.

The obtained solution can be maintained for about 24 hours to about 72 hours, for example about 30 hours, preferably at about room temperature.

Figure 27:
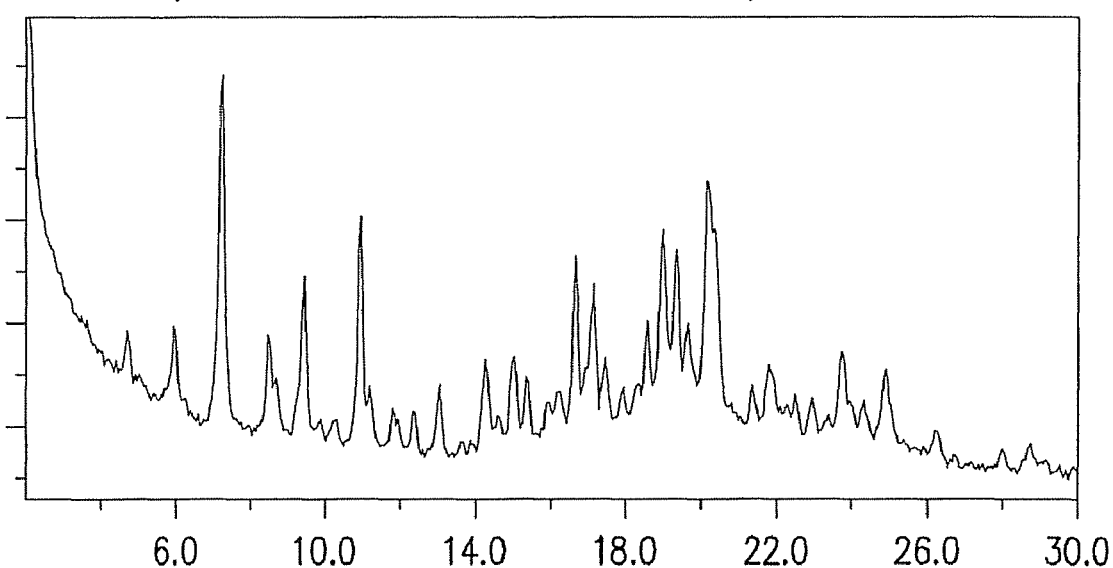
FIG. 27 represents an XRPD pattern of crystalline Form S2 of aliskiren hemisuccinate.

In one embodiment, the invention provides aliskiren hemisuccinate, designated S2, characterized by data selected from the group consisting of an XRPD pattern with peaks at about 4.6, 5.9, 7.1, 9.3 and 10.9±0.2 degrees two-theta; an XRPD pattern as depicted in FIG. 27; and combination thereof.

Form S2 can be further characterized by additional peaks at about 17.1, 18.7, 19.4, and 20.1±0.2 degrees two-theta.

In another embodiment, Form S2 is characterized by an XRPD pattern with peaks at about 7.2, 9.5, 10.9, 14.2 and 16.6±0.3 degrees two-theta.

In another embodiment, Form S2 is characterized by an XRPD pattern with peaks at about 4.7, 6.0, 7.2, 8.5, 9.5, 10.9, 14.2, 15.0, 16.6 and 17.1±0.3 degrees two-theta.

Aliskiren hemisuccinate Form S2 typically has one or more improved characteristics compared to the prior art forms, especially compared with the known aliskiren hemifumarate forms, such as higher crystallinity, solubility, dissolution rate, morphology, stability to polymorphic conversion, a lower degree of hygroscopicity, storage stability, flowability, and advantageous processing and handling characteristics such as compressibility and/or bulk density. Aliskiren hemisuccinate Form S2 preferably has an advantageous crystallinity or solubility compared to known forms of aliskiren salts (especially compared with known aliskiren hemifumarate forms), and in particular aliskiren hemisuccinate Form S2 has a crystal habit that enables easy handling and processing, and thus can be easily compressed. The prior art aliskiren hemifumarate forms are less desirable from a formulation perspective, due to their needle-shaped crystal habit. Such a crystal habit affects the processability of the active agent, and can cause problems, e.g., with compression. Particularly, the aliskiren hemisuccinate Form S2 of the present invention does not have needle-shaped crystals, and retains a good degree of crystallinity. Therefore, Form S2 is especially useful for processing into formulations.

Form S2 can be prepared by a process comprising providing a solution of aliskiren hemisuccinate in acetonitrile, further stirring the solution to obtain a suspension and recovering the crystalline material.

The aliskiren hemisuccinate can be used in an amount of about 20 mg to about 100 mg, for example about 100 mg per ml of solvent.

The obtained solution can be maintained for about 24 hours to about 72 hours, for example about 30 hours, preferably at about room temperature.

Form S2 can be recovered from the obtained suspension by filtration.

The obtained S2 can be further dried. Drying can be carried out under a pressure of less than one atmosphere (reduced pressure), including a pressure of less than about 100 mm Hg.

Drying can be carried out by heating, with or without reducing the pressure, at about 40° C. to about 80° C., about 40° C. to about 60° C., about 40° C. to about 50° C., for example, at about 40° C. The obtained precipitate can be dried for about 16 hours to about 72 hours, for about 16 hours to about 48 hours, for about 16 hours to about 24 hours.

Figure 21:
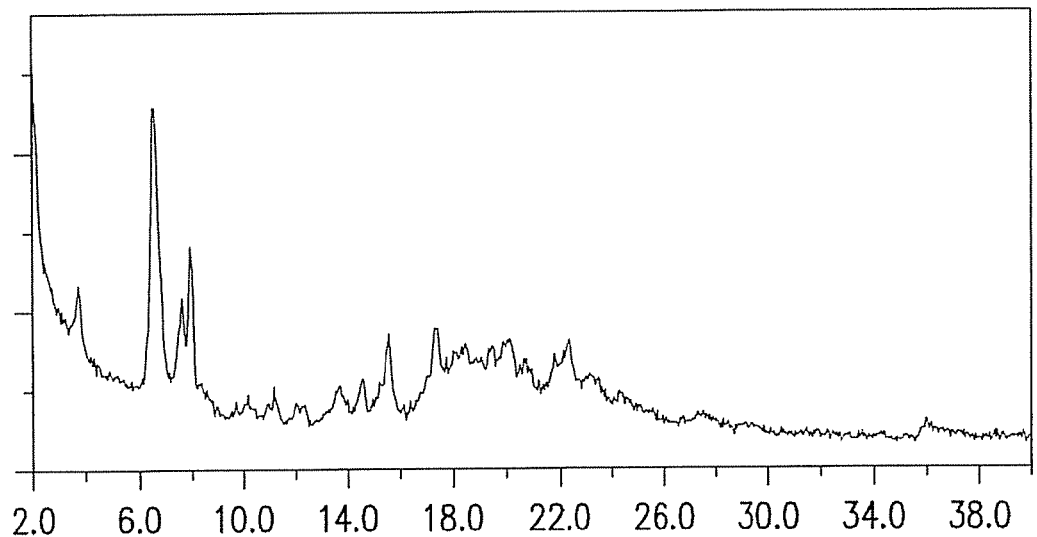
FIG. 21 represents an XRPD pattern of crystalline Form S3 of aliskiren hemisuccinate obtained according to example 9.
Figure 22:
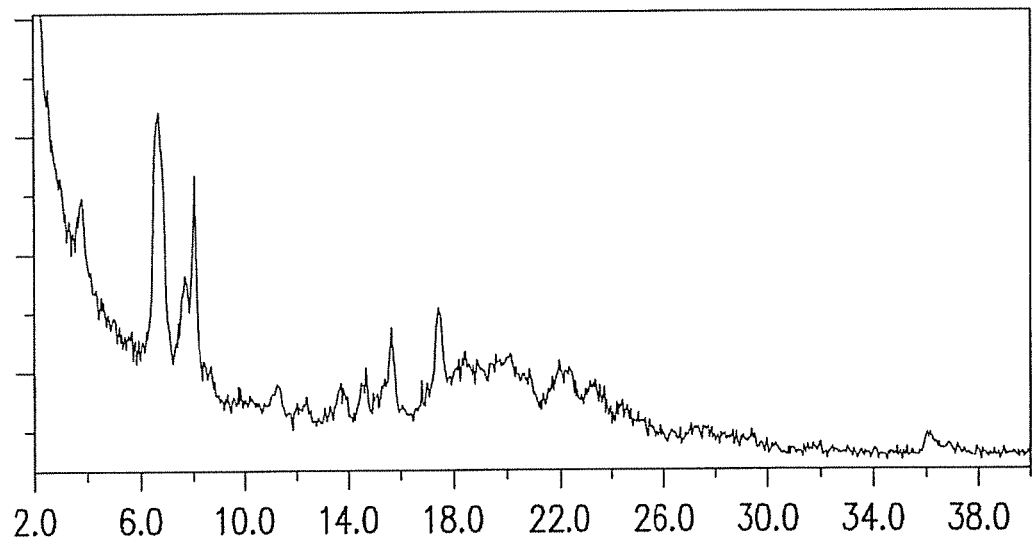
FIG. 22 represents an XRPD pattern of crystalline Form S3 of aliskiren hemisuccinate obtained according to example 11.

In one embodiment, the invention provides Form S3 of aliskiren hemisuccinate characterized by data selected from the group consisting of an XRPD pattern with peaks at about 6.7, 8.0, 15.6 and 17.4±0.3 degrees two-theta; an XRPD pattern as depicted in FIG. 21; and combination thereof.

Alternatively, Form S3 can be characterized by an XRPD pattern with peaks at about 3.8, 6.7, 7.7, 8.0, 11.2, 13.7, 14.6, 15.6 and 17.4±0.3 degrees two-theta.

Aliskiren hemisuccinate Form S3 typically has one or more improved characteristics compared to the prior art forms, especially compared with the known aliskiren hemifumarate forms, such as higher crystallinity, solubility, dissolution rate, morphology, stability to polymorphic conversion, a lower degree of hygroscopicity, storage stability, flowability, and advantageous processing and handling characteristics such as compressibility and/or bulk density. Aliskiren hemisuccinate Form S3 preferably has an advantageous crystallinity or solubility compared to known forms of aliskiren salts (especially compared with known aliskiren hemifumarate forms), and in particular aliskiren hemisuccinate Form S3 has a crystal habit that enables easy handling and processing, and thus can be easily compressed. The prior art aliskiren hemifumarate forms are less desirable from a formulation perspective, due to their needle-shaped crystal habit. Such a crystal habit affects the processability of the active agent, and can cause problems, e.g., with compression. Particularly, the aliskiren hemisuccinate Form S3 of the present invention does not have needle-shaped crystals, and retains a good degree of crystallinity. Therefore, Form S3 is especially useful for processing into formulations.

Form S3 can be prepared by a process comprising drying Form S1.

Drying can be carried out under a pressure of less than one atmosphere (reduced pressure), including a pressure of less than about 100 mm Hg. Drying can be carried out by heating, with or without reducing the pressure, at about 40° C. to about 80° C., at about 40° C. to about 60° C., at about 40° C. to about 50° C., for example, at about 50° C. The obtained precipitate can be dried for about 16 hours to about 72 hours, for about 16 hours to about 48 hours, for about 16 hours to about 24 hours.

Form S3 can be prepared by another process comprising providing a suspension of amorphous aliskiren hemisuccinate in cyclopentylmethyl then, further stirring the suspension and recovering the crystalline material. The obtained precipitate can be further dried.

Drying can be carried out under a pressure of less than one atmosphere (reduced pressure), including a pressure of less than about 100 mm Hg. Drying can be carried out by heating, with or without reducing the pressure, at about 40° C. to about 80° C., at about 40° C. to about 60° C., at about 40° C. to about 50° C., for example, at about 50° C. The obtained precipitate can be dried for about 16 hours to about 72 hours, for about 16 hours to about 48 hours, for about 16 hours to about 24 hours.

The aliskiren hemisuccinate can be used in an amount of about 20 mg to about 100 mg, for example, about 100 mg per ml of solvent.

The obtained solution can be maintained for about 24 hours to about 72 hours, preferably at about room temperature.

Figure 23:
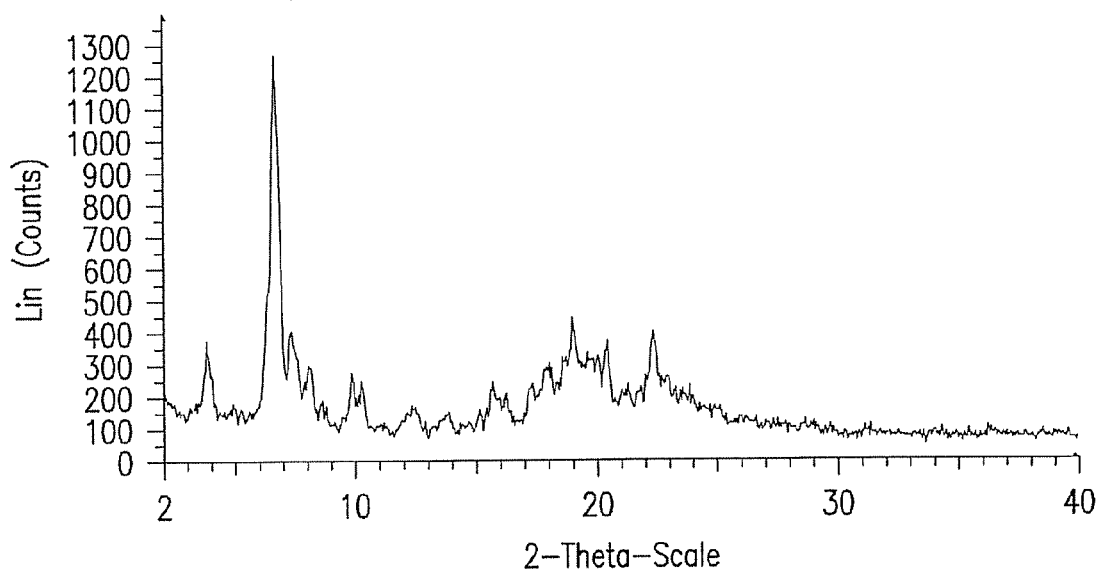
FIG. 23 represents an XRPD pattern of crystalline Form S4 of aliskiren hemisuccinate.

In another embodiment, the invention provides Form S4 of aliskiren hemisuccinate characterized by data selected from the group consisting of an XRPD pattern with peaks at about 9.8, 10.2, 19.0, 20.4 and 22.3±0.3 degrees two-theta; an XRPD pattern as depicted in FIG. 23; and combination thereof.

In another embodiment, Form S4 is characterized by an XRPD pattern with peaks at about 3.8, 7.3, 9.8, 10.2, 16.2, 17.3, 19.0, 20.4 and 22.3±0.3 degrees two-theta.

Aliskiren hemisuccinate Form S4 typically has one or more improved characteristics compared to the prior art forms, especially compared with the known aliskiren hemifumarate forms, such as higher crystallinity, solubility, dissolution rate, morphology, stability to polymorphic conversion, a lower degree of hygroscopicity, storage stability, flowability, and advantageous processing and handling characteristics such as compressibility and/or bulk density. Aliskiren hemisuccinate Form S4 preferably has an advantageous crystallinity or solubility compared to known forms of aliskiren salts (especially compared with known aliskiren hemifumarate forms). In particular aliskiren hemisuccinate Form S4 has a crystal habit that enables easy handling and processing, and thus can be easily compressed.

Form S4 can be prepared by a process comprising slurrying amorphous aliskiren hemisuccinate in ethyl acetate and recovering the crystalline material.

The aliskiren base is used in an amount of about 20 mg to about 100 mg, for example, about 100 mg per ml of alcohol.

The obtained slurry can be maintained for about 24 hours to about 72 hours, for example, about 30 hours, preferably at about room temperature.

Figure 24:
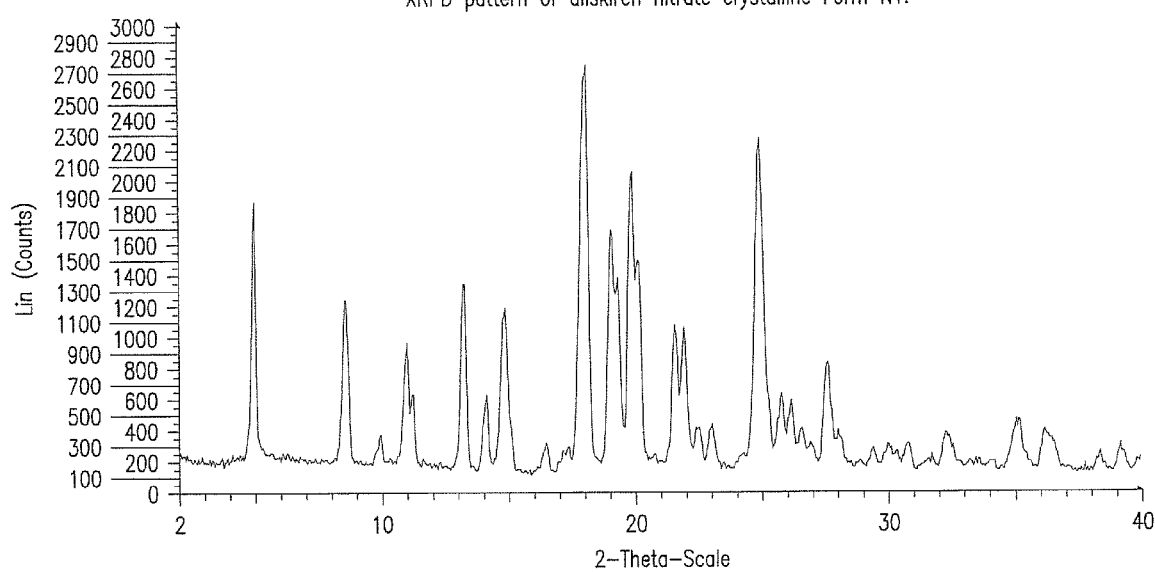
FIG. 24 represents an XRPD pattern of crystalline Form N1 of aliskiren nitrate.

In one embodiment, the invention provides aliskiren nitrate, designated N1, characterized by data selected from the group consisting of an XRPD pattern with peaks at about 4.9, 8.5, 13.2, 14.8 and 18.1±0.2 degrees two-theta; an XRPD pattern as depicted in FIG. 24; and combination thereof.

Form N1 can be further characterized by additional peaks at about 11.0, 19.1, 19.9, 21.9 and 24.9±0.2 degrees two-theta.

Aliskiren nitrate N1 can be prepared by a process comprising slurrying aliskiren nitrate in isopropanol and recovering the crystalline material; wherein aliskiren nitrate is dissolved in a $C_1$-$C_2$ alcohol and prior to the slurrying, the alcohol is removed from the aliskiren nitrate solution.

The solvent in the above process describing the preparation of Form N1 can be removed by filtration and drying.

Optionally, the slurried aliskiren nitrate in isopropanol is maintained in an open container at room temperature to obtain the crystalline form aliskiren nitrate N1.

Figure 25:
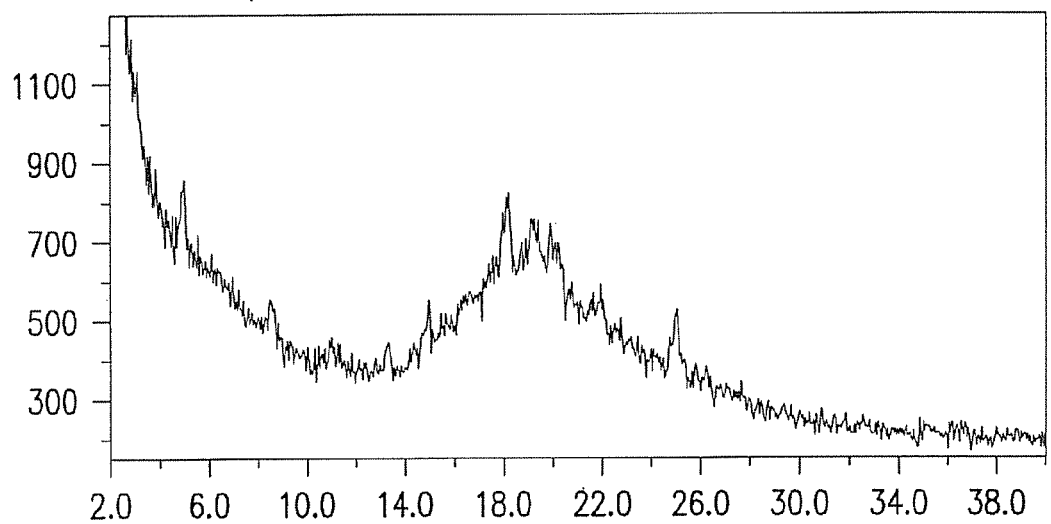
FIG. 25 represents an XRPD pattern of crystalline Form M1 of aliskiren hemimaleate.

In one embodiment, the invention provides aliskiren hemimaleate, designated M1, characterized by data selected from the group consisting of an XRPD pattern with peaks at about 5.0, 8.5, 13.3, 15.0 and 18.2±0.2 degrees two-theta; an XRPD pattern as depicted in FIG. 25; and combination thereof.

Form M1 can be further characterized by an XRPD pattern containing additional peaks at about 11.0, 19.2, 19.9, 21.9 and 25.0±0.2 degrees two-theta.

Aliskiren hemimaleate M1 can be prepared by a process comprising slurrying amorphous aliskiren hemimaleate in diisopropyl ether and recovering the crystalline material.

The solvent in the above process describing the preparation of Form M1 can be removed by filtration and drying.

The aliskiren base is used in an amount of about 20 mg to about 100 mg, for example, about 100 mg per ml of alcohol.

The obtained slurry can be maintained for about 24 hours to about 72 hours, for example, about 30 hours, preferably at about room temperature.

Figure 26:
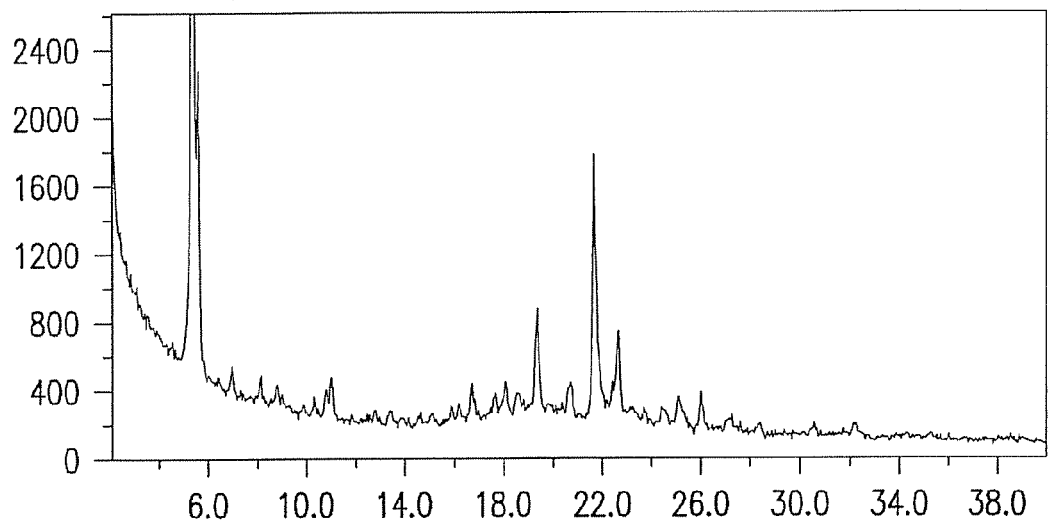
FIG. 26 represents an XRPD pattern of crystalline Form I1 of aliskiren hydrogen citrate.

In one embodiment, the invention provides aliskiren hydrogen citrate, designated I1, characterized by data selected from the group consisting of an XRPD pattern with peaks at about 5.4, 5.6, 7.0, 11.0 and 22.6±0.2 degrees two-theta; and an XRPD pattern as depicted in FIG. 26; and combination thereof.

Form I1 can be further characterized by an XRPD pattern containing additional peaks at about 8.1, 8.8, 16.7, 18.1, 19.3, 20.7 and 21.7±0.2 degrees two-theta.

Aliskiren hydrogen citrate I1 can be prepared by a process comprising providing a solution of amorphous aliskiren hydrogen citrate in acetonitrile, further stirring the solution to obtain a suspension and recovering the crystalline material.

The aliskiren base is used in an amount of about 20 mg to about 100 mg, for example, about 100 mg per ml of alcohol.

The obtained slurry can be maintained for about 24 hours to about 72 hours, for example, about 30 hours, preferably at about room temperature.

In one embodiment, the $C_1$-$C_2$ alcohol used in any of the processes described above is ethanol or methanol. Preferably, ethanol is used.

The removal step described in any of the processes described above can be performed by conventional techniques, such as filtration and drying, evaporation or evaporation by using an inert gas flow. Evaporation can be performed under atmospheric pressure or under vacuum at about 20° C. to about 40° C. Preferably, when the process is performed using slurrying, the removal is by filtration.

The invention further encompasses a pharmaceutical formulation comprising the amorphous or crystalline forms of pharmaceutically acceptable compounds of aliskiren. This pharmaceutical composition may additionally comprise at least one pharmaceutically acceptable excipient.

The invention further encompasses a pharmaceutical composition comprising the amorphous form or the crystalline form made by the processes of the present invention, and one or more pharmaceutically acceptable excipients.

The present invention further encompasses a process for preparing a pharmaceutical formulation comprising combining the amorphous form or the crystalline form of the present invention with at least one pharmaceutically acceptable excipient.

In another embodiment, the present invention provides a method for inhibiting the enzyme renin and treating patients with hypertension comprising administering to a patient in need thereof a therapeutically effective amount of the above crystalline or amorphous forms of pharmaceutically acceptable compounds of aliskiren.

Having thus described the invention with reference to particular preferred embodiments and illustrative examples, those in the art can appreciate modifications to the invention as described and illustrated that do not depart from the spirit and scope of the invention as disclosed in the specification. The examples are set forth to aid in understanding the invention but are not intended to, and should not be construed to limit its scope in any way.

EXAMPLES

XRPD analyses were performed using one of the following:
1. ARL (SONTAG) X-ray powder diffractometer model X'TRA-019, CuKα radiation, Peltier detector, round standard aluminum sample holder with round zero background plate was used. Scanning parameters: Range: 2-40 deg 2, continuous scan, Rate: 3 deg/min (FIGS. 7, 8, 15, 16, 17, 21, 22, 25, 26).
2. Bruker X-Ray powder diffractometer model D8 advance, CuKα radiation, equipped with LynxEye position sensitive detector. Scan range: 2-40°. Step size: 0.05°. Time per step: 5.2 seconds (FIGS. 1, 2, 3, 4, 5, 6, 9, 10, 11, 12, 13, 14, 18, 19, 20, 23, 24).

Example 1

General Procedure for Preparation of Aliskiren Compounds

An ethanolic solution of acid (selected from the list of acids detailed in Table 1 attached below) was added to a stirred 0.1M ethanolic solution of aliskiren base (AKN) (5 ml, 0.5 mmol), and the solution was stirred for an hour at room temperature. Ethanol was evaporated under vacuum at 40° C., and the solid was dried under vacuum at the same temperature overnight. The solid was analyzed by XRPD.

Table 1 summarizes the various experiments performed to obtain aliskiren compounds using different acids and their XRPD interpretation:

TABLE 1

| Acid/mmol | Compound obtained | XRPD |
|---|---|---|
| Maleic/0.25 | AKN hemimaleate | Amorphous |
| Maleic/0.5 | AKN monomaleate | Amorphous |
| Succinic/0.25 | AKN hemisuccinate | Amorphous |
| racemic Tartaric/0.25 | AKN hemitartrate | Amorphous |
| D,L-Tartaric/0.5 | AKN monotartrate | Amorphous |
| Sulfuric/0.5 | AKN hydrogen sulfate | Amorphous |
| Ortho-phosphoric/0.33 | AKN hydrogen phosphate | Amorphous |
| Ortho-phosphoric/0.5 | AKN dihydrogen phosphate | Amorphous |
| Hydrogen chloride/0.5 | AKN hydrochloride | Amorphous |
| Hydrogen bromide/0.5 | AKN hydrobromide | Amorphous |
| Citric/0.5 | AKN dihydrogen citrate | Amorphous |
| Citric/0.33 | AKN hydrogen citrate | Amorphous |
| Citric/0.17 | AKN citrate | Amorphous |
| D-Malic/0.5 | AKN monomalate | Amorphous |
| D-Malic/0.25 | AKN hemimalate | Amorphous |

Example 2

Preparation of Polymorphic Form of Aliskiren Hydrochloride C1

Amorphous aliskiren hydrochloride (50 mg) was suspended in 0.5 ml of isobutyl acetate. The suspension was stirred at room temperature for 3 days. The solid was filtered and analyzed by XRPD.

Example 3

Preparation of Polymorphic Form of Aliskiren Hydrochloride C2

Amorphous aliskiren hydrochloride (50 mg) was suspended in 0.5 ml of toluene. The suspension was stirred at room temperature for 3 days. The solid was filtered and analyzed by XRPD.

Example 4

Preparation of Polymorphic Form of Aliskiren Hydrochloride C2

Amorphous aliskiren hydrochloride (50 mg) was suspended in 0.5 ml of dimethylcarbonate. The suspension was stirred at room temperature for 3 days. The solid was filtered, dried at 50° C. under vacuum overnight and analyzed by XRPD.

Example 5

Preparation of Polymorphic Form of Aliskiren Hydrochloride C2

Amorphous aliskiren hydrochloride (50 mg) was stirred with 0.5 ml of chlorobenzene at room temperature for 3 days to give a suspension. The solid was filtered, dried at 50° C. under vacuum overnight and analyzed by XRPD

Example 6

Preparation of Polymorphic Form of Aliskiren Hydrochloride C3

Aliskiren hydrochloride C1 was prepared according to example 2 and further dried at 40° C. under vacuum overnight and analyzed by XRPD.

Example 7

Preparation of Polymorphic Form of Aliskiren Hemisuccinate S4

Amorphous aliskiren hemisuccinate (50 mg) was suspended with 0.5 ml of ethyl acetate at room temperature for 30 hours. The solid was filtered and analyzed by XRPD.

Example 8

Preparation of Polymorphic Form of Aliskiren Hemisuccinate S1

Amorphous aliskiren hemisuccinate (50 mg) was stirred with 0.5 ml of dimethylcarbonate at room temperature for 30 hours to give a suspension. The solid was filtered and analyzed by XRPD.

Example 9

Preparation of Polymorphic Form of Aliskiren Hemisuccinate S3

Aliskiren hemisuccinate S1 was prepared according to example 8 and further dried at 50° C. under vacuum overnight and analyzed by XRPD.

Example 10

Preparation of Polymorphic Form of Aliskiren Hemisuccinate S1

Amorphous aliskiren hemisuccinate (50 mg) was stirred with 0.5 ml of diethylcarbonate at room temperature for 30 hours to give a suspension. The solid was filtered and analyzed by XRPD.

Example 11

Preparation of Polymorphic Form of Aliskiren Hemisuccinate S3

Aliskiren hemisuccinate S3 was prepared according to example 10 and further dried at 50° C. under vacuum overnight and analyzed by XRPD.

Example 12

Preparation of Polymorphic Form of Aliskiren Hemisuccinate S2

Amorphous aliskiren hemisuccinate (50 mg) was stirred with 0.5 ml of acetonitrile at room temperature for 30 hours to give a suspension. The solid was filtered, dried at 50° C. under vacuum overnight and analyzed by XRPD.

Example 13

Preparation of Polymorphic Form of Aliskiren Hemisuccinate 83

Amorphous aliskiren hemisuccinate (50 mg) was stirred with 0.5 ml of cyclopentylmethyl ether at room temperature for 30 hours to give a suspension. The solid was filtered and analyzed by XRPD.

Example 14

Preparation of Polymorphic Form of Aliskiren Hemisuccinate Form S1

Amorphous aliskiren hemisuccinate (50 mg) was stirred with 0.5 ml of diethoxymethane at room temperature for the weekend to give an unstirrable suspension. Diethoxymethane (0.5 ml) was added and the solid was filtered and analyzed by XRPD.

Example 15

Preparation of Polymorphic Form of Aliskiren Nitrate N1

An ethanolic solution of nitric acid (0.1 M solution, 6 ml, 0.6 mmol) was added to a stirred 0.1M ethanolic solution of aliskiren base (AKN) (6 ml, 0.6 mmol), and the solution was stirred for an hour at room temperature. Ethanol was evaporated under vacuum at 40° C. to dryness. The solid was suspended in 1 ml of isopropanol. After an hour the suspension became unstirrable and 1 ml of isopropanol was added. The suspension was stirred at room temperature overnight. The solid was filtered and dried at 40° C. under vacuum overnight. The wet and dry samples were analyzed by XRPD. Form N1 for Wet and Dry Samples.

The mother liquor was kept in an open glass for a day and isopropanol was evaporated. Obtained crystals were analyzed by XRPD.

Example 16

Preparation of Polymorphic Form of Aliskiren Hemimaleate M1

Amorphous aliskiren hemimaleate (50 mg) was suspended with 0.5 ml of diisopropyl ether at room temperature for 30 hours. The solid was filtered, dried at 50° C. under vacuum overnight and analyzed by XRPD.

Example 17

Preparation of Polymorphic Form of Aliskiren Hydrogen Citrate I1

Amorphous aliskiren hydrogen citrate (50 mg) was stirred with 0.5 ml of acetonitrile at room temperature for 30 hours to give a suspension. The solid was filtered and analyzed by XRPD.

What is claimed is:

1. A crystalline form of aliskiren hemisuccinate designated Form S1, characterized by the data selected from the group consisting of an XRPD pattern with peaks at about 3.7, 6.7, 7.3 and 8.5±0.2 degrees two-theta; and an XRPD pattern as depicted in FIG. 18.

2. A crystalline form of aliskiren hemisuccinate designated Form S2, characterized by the data selected from the group consisting of an XRPD pattern with peaks at about 4.6, 5.9, 7.1, 9.3 and 10.9±0.2 degrees two-theta; and an XRPD pattern as depicted in FIG. 27.

3. A crystalline form of aliskiren hemisuccinate designated Form S3, characterized by the data selected from the group consisting of an XRPD pattern with peaks at about 6.7, 8.0, 15.6 and 17.4±0.3 degrees two-theta; an XRPD pattern as depicted in FIG. 21.

4. A crystalline form of aliskiren hemisuccinate designated Form S4, characterized by the data selected from the group consisting of an XRPD pattern with peaks at about 9.8, 10.2, 19.0, 20.4 and 22.3±0.3 degrees two-theta; an XRPD pattern as depicted in FIG. 23.

5. A pharmaceutical composition comprising the crystalline form of aliskiren hemisuccinate of any one of claims 1-4, and at least one pharmaceutically acceptable excipient.

6. A process for preparing a pharmaceutical formulation comprising combining the crystalline form of aliskiren hemisuccinate of any one of claims 1-4, with at least one pharmaceutically acceptable excipient.

7. A crystalline form of aliskiren hemisuccinate selected from:

Form S1, characterized by data selected from an XRPD pattern with peaks at about 3.7, 6.7, 7.3 and 8.5±0.2 degrees two-theta; and an XRPD pattern as depicted in FIG. 18;

Form S2, characterized by data selected from an XRPD pattern with peaks at about 4.6, 5.9, 7.1, 9.3 and 10.9±0.2 degrees two-theta; and an XRPD pattern as depicted in FIG. 27;

Form S3, characterized by data selected from an XRPD pattern with peaks at about 6.7, 8.0, 15.6 and 17.4±0.3 degrees two-theta; and an XRPD pattern as depicted in FIG. 21; and Form S4, characterized by data selected from an XRPD pattern with peaks at about 9.8, 10.2, 19.0, 20.4 and 22.3±0.3 degrees two-theta; and an XRPD pattern as depicted in FIG. 23.

* * * * *